United States Patent
Lukaczer et al.

(10) Patent No.: US 6,352,712 B1
(45) Date of Patent: *Mar. 5, 2002

(54) DIETARY SUPPLEMENTS FOR TREATING FATIGUE-RELATED SYNDROMES

(76) Inventors: Daniel O. Lukaczer, 5820 98 th Ave. North; Gary K. Darland, 1718 Clorindi Cir. NW.; DeAnn J. Liska, 6200 Soundview Dr., #D103; Tracey A. Irving, 3802 64th Avenue Ct. NW., all of Gig Harbor, WA (US) 98335; Jeffrey S. Bland, 957 11th La., Fox Island, WA (US) 98333

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/303,779

(22) Filed: Apr. 30, 1999

(51) Int. Cl.[7] .............................. A61K 9/14; A23L 1/29
(52) U.S. Cl. ........................................ 424/439; 424/489
(58) Field of Search .............................. 424/195.1, 489, 424/439

(56) References Cited

U.S. PATENT DOCUMENTS 5,904,924 A * 5/1999 Gaynor et al. ............ 424/195.1

OTHER PUBLICATIONS

UltraBalance Products, "A Patient Guide: UltraClear, UltraClear Plus, UltraClear Sustain," pp. 1–49, 1999.
UltraBalance Products, "Program Description Booklet for Weight Management and Food Allergy Testing," pp. 1–44, 1997.
UltraBalance Products, "UltraClear Metabolic Detoxification Program," 1998.
Rigden, S. et al., "Management of Chronic Fatigue Symptoms by Tailored Nutritional Intervention Using a Program Designed to Support Hepatic Detoxification".
Rigden, S. et al., "Evaluation of the Effect of a Modified Entero–Hepatic Resuscitation Program in Chronic Fatigue Syndrome Patients," *Journal of Advancement in Medicine*, 11:4, pp. 247–261, 1998.
Bland, J.S. et al., "Nutritional Upregulation of Hepatic Detoxication Enzymes," *Journal of Applied Nutrition*, 44:3–4, pp. 1–15, 1992.
Bland, J.S. et al., "A Medical Food–Supplemented Detoxification Program in the Management of Chronic Health Problems," *Alternative Therapies*, 1:5, 1995.
Liska, D.J. et al., "Antigenicity of Rice Protein Concentrate and Rice Flours," *Functional Medicine Research Center*, 102, 1997.
Liska, D.J. et al., "Evaluating the Benefits of Functional Foods," *New Technologies for Healthy Foods and Nutraceuticals*, 1997 (in press).
HealthComm International, Inc., "Remove, Replace, Reinoculate, Repair: The 4R Gastorintestinal Support Program," technical bulletin, 1998.
Rigden, S., "Entero–Hepatic Resuscitation Program for CFIDS," *The CFIDS Chronicle*, pp. 46–49, 1995.
Rice–Evans, C.A. et al., "Structure–Antioxidant Activity Relationships of Flavonoids and Phenolic Acids," *Free Radical Biology & Medicine* 20:7, pp. 933–956, 1996.
Sreejayan, N. et al., "Free Radical Scavenging Activity of Curcuminoids," *Arzneim–Forsch./Drug Res.* 46(I):2, pp. 169–171, 1996.
Haenen, G.R.M.M. et al., "Peroxynitrite Scanvenging by Flavonoids," *Biochemical and Biophysical Research Communications 236*, pp. 591–593, 1997.
Sato, M. et al., "Quercetin, a Bioflavonoid, Inhibits the Induction of Interleukin 8 and Monocyte Chemoattractant Protein–1 Expression by Tumor Necrosis Factor–60 in Cultured Human Synovial Cells," *The Journal of Rheumatology* 24:9, pp. 1680–1684, 1997.
Ringbom, T. et al., "Ursolic Acid from *Plantago major*, a Selective Inhibitor of Cycloosygenase–2 Catalyzed Prostaglandin Biosynthesis," *J. Nat. Prod. 61*, pp. 1212–1215, 1998.

* cited by examiner

Primary Examiner—Thurman K. Page
Assistant Examiner—P. McQueeney
(74) *Attorney, Agent, or Firm*—Knobbe, Martens, Olson & Bear, LLP

(57) ABSTRACT

The present invention provides dietary supplements, medical foods and methods effective to ameliorate at least one of the symptoms, preferably all of the symptoms, of a fatigue-related syndrome, such as fibromyalgia. The dietary supplements of the present invention include rosemary, curcumin and at least one component selected from the group consisting of quercetin and rutin. The medical foods of the present invention include rosemary, at least one macronutrient selected from the group consisting of protein, carbohydrate and fat, and at least one member of the group consisting of quercetin, curcumin and rutin. The methods of the present invention include the step of administering to a person suffering from a fatigue-related syndrome an effective amount of a dietary supplement or medical food of the present invention.

40 Claims, No Drawings

DIETARY SUPPLEMENTS FOR TREATING FATIGUE-RELATED SYNDROMES

FIELD OF THE INVENTION

The present invention relates to dietary supplements and medical foods for treating fatigue-related syndromes. The compositions of the present invention include rosemary.

BACKGROUND OF THE INVENTION

In 1948, the World Health Organization defined health as not only the absence of disease, but also the presence of physical, mental, and social well-being. (Constitution of the World Health Organization. In: World Health Organization, Handbook of Basic Documents. 5th ed. Geneva: Palais des Nations, 3–20 (1952)). The status of a patient's physical, mental, and social functioning is often referred to in the literature as quality-of-life and is used as a measure of health outcome. In the past 25 years, there has been a nearly exponential increase in the evaluation of quality-of-life as a technique of clinical research as a component of determining clinical benefit from an intervention protocol. For example, in 1973, only five articles listed quality-of-life as a key word in the Medline database, whereas in the subsequent four years there were successively 195, 273, 490, and 1,252 such articles. (Testa MA and Simonson DC, *N Eng J Med.* 334:835–840 (1996). In 1998, approximately 3,724 articles listed quality-of-life as a key word. Thus, the health outcome, or quality-of-life, associated with a clinical intervention has been recognized as an important tool in measuring effectiveness and costs of medical care. (Wilson IB and Cleary PD., *JAMA.*, 273:59–65 (1995)).

Extensive research has resulted in the development of instruments that measure health outcome using quality-of-life tools that follow academically well-established and statistically validated psychometric principles. (Ware J E Jr., *J Chronic Dis.*, 40:473–480 (1987); Spilker B., Quality of Life and Pharmacoeconomics in Clinical Trials, 2nd ed. Philadelphia, Pa: Lippincott-Raven Co; 1995.) One such tool is the SF-36 (Short form-36), which has been widely used in clinical trials and in clinical practice to assess health outcome. (Clancy CM and Eisenberg J M, *Science*, 282:245–246 (1998)). The SF-36 was derived from the Medical Outcomes Study, which involved 11,336 patients from 523 different clinical sites. (Ware J E, Sherbourne C D, Davies A R. Developing and testing the MOS 20-item short-form health survey. In: Stewart AL and Ware J E, eds., Measuring functioning and well-being: The Medical Outcomes Study approach. Durham, N.C.: University Press, 277–290 (1992); Ware J E. SF-36 Health Survey: manual and interpretation guide. Boston, Mass.: Nimrod Press; 2:1–3:22 (1993)). The validity and reliability of the SF-36 has been proven in several studies in which researchers tested internal consistency, within subject reliability, and differentiation between patient populations. (McHorney CA, et al., *Medical Care*, 31:247–263 (1993); McHorney CA, et al., *Medical Care*, 30:S253–S265 (1992); Jenkinson C, et al., *Br Med J.*, 306:1436–1440 (1993); Brazier J E, et al., *Br Med J.* 305:160–164 (1992)). The SF-36 has been shown to predict the course of depression during a two-year study, and to be lower overall in patients who experience chronic health disorders. (Wells K B, et al., *Archives General Psychiatry*, 49:788–794 (1992); Schlenk E A, et al., *Quality of Life Res.*, 7:57–65 (1998)).

The SF-36 is a 36-item questionnaire that assesses eight dimensions of health outcome: physical functioning, role-physical, bodily pain, general health, vitality, social functioning, role-emotional, and mental health. Results from the questionnaire can be reported as a relative number on a scale of 0 to 100, in which 100 is the highest or most functional and 0 is the most compromised for that category of functioning. A summary of the meaning of high and low scores for each category is shown-in Table 1.

TABLE 1

Description of Very High and Very Low Scores for the Eight Categories of the MOS SF-36 Questionnaire.

| SF-36 Category | Interpretation of a Low Score | Interpretation of a High Score |
| --- | --- | --- |
| Physical Functioning (PF) | Limited in performing all physical activities including bathing or dressing due to health | Performs all types of physical activities including the most vigorous without limitations due to health |
| Role-Physical (RP) | Problems with work or other daily activities as a result of physical health | No problems with work or other daily activities as a result of physical health |
| Bodily Pain (BP) | Very severe and extremely limiting pain | No pain or limitations due to pain |
| General Health (GH) | Evaluates personal health as poor and believes it is likely to get worse | Evaluates personal health as excellent |
| Vitality (VT) | Feels tired and worn out all of the time | Feels full of pep and energy all of the time |
| Social Functioning (SF) | Extreme and frequent interference with normal social activities due to physical or emotional problems | Performs normal social activities without interference due to physical or emotional problems |
| Role-Emotional (RE) | Problems with work or other daily activities as a result of emotional problems | No problems with work or other daily activities as a result of emotional problems |
| Mental Health (MH) | Feelings of nervousness and depression all of the time | Feels peaceful, happy, and calm all of the time |

The latter half of the twentieth century has been characterized by an increasing prevalence of chronic disorders. Indeed, seven of the ten leading causes of death in the USA are chronic in nature, accounting for 72% of the deaths from all causes. (National Center for Health Statistics. Health, United States, 1995. Hyattsville, Md.: Public Health Service, 1995.) Chronic disorders such as rheumatic disorders, chronic pain, and fatigue contribute to the 6% of the population that is impaired to some extent in the conduct of major life activities such as work, school, and self-care. (US Department of Health and Human Services, Public Health Service. Healthy People 2000: National Health Promotion and Disease Prevention Objectives. Hyattsville, Md.: Public Health Service; 1991.) Health care use also appears to be substantial for patients with chronic conditions. For example, patients with chronic fatigue syndrome (CFS), fibromyalgia (FM), and multiple chemical sensitivities (MCS) have been shown to visit medical care facilities on average 22.1, 39.7, and 23.3 times per year, respectively. (Buchwald D, Garrity D., *Arch Intern Med.*, 154:2049–2053 (1994)).

In chronic conditions such as rheumatic disorders, fatigue and energy-deficit disorders, and chronic pain, biological and physiological factors have an inconsistent relationship to symptoms. (Wilson IB, Cleary PD., *JAMA*, 273:59–65 (1995)). Therefore, they are difficult to measure by laboratory values. In fact, in clinical practice, anywhere from 30% to 80% of patients who see a physician may have conditions for which no physiological or organic cause is found after routine investigation. (Wilson IB and Cleary P D, *JAMA*, 273:59–65 (1995)).

For example, the term fibromyalgia (FM) refers to an illness whose major characteristics are widespread chronic pain and the physical finding of pain in specifically located tender points. (Wolfe F, et al., The American College of Rheumatology 1990 criteria for the classification of fibromyalgia. *Arthritis Rheumatology*, 33:160–172 (1990)). Fibromyalgia patients also commonly report morning stiffness, fatigue, and sleep disturbances. A patient presenting with fibromyalgia sometimes reports peripheral athralgias, which can be confused with rheumatoid arthritis. (Goldenberg D L., *Current Opinions in Rheumatology*, 5:199–208 (1993)). However, fibromyalgia is commonly accepted in the field as pain not associated with inflammation nor joint dysfunction, whereas athralgias are considered inflammatory joint disorders.

Another example of a chronic condition is "chronic fatigue syndrome" (CFS). Clinical diagnosis of CFS requires that the patient show evidence of fatigue lasting beyond 6 months, as well as having eight or more of the following minor symptoms: fever, sore throat, myalgia, muscle weakness (which may be exacerbated by exercise), athralgia, lymphadenopathy, sleep disturbance, headaches, acute or subacute onset, and neuropsychological symptoms. (Holmes G P, et al., *Ann Intern Med.*, 108:387–389 (1988)). Other chronic conditions include idiotypic fatigue, myofascial pain syndrome, for which no definition exists, as well as autoimmune disorders, asthma, and gastrointestinal disorders such as irritable bowel syndrome.

In these chronic conditions, pain and fatigue are often suffered over many years without correlation to a diagnosable or definable acute or chronic disease. Therefore, without anatomical or physical correlation, a patient's response to therapy must be monitored by measuring the level of symptoms they report over a period of time. The MOS SF-36 questionnaire is particularly suited to this type of analysis. For example, patients with chronic disorders such as fibromyalgia have been reported to score lower than the norm in several categories of the MOS SF-36, including bodily pain, role-physical, role-emotional, and vitality (Table 2 where numbers in brackets represent standard deviations).

TABLE 2

MOS SF-36 Scores for US Population and Fibromyalgia Patients.

| SF-36 Category | US Norm - Females (n = 1,412) | US Norm - Males (n = 1,055) | Fibromyalgia (n = 18) |
|---|---|---|---|
| Physical Functioning (PF) | 81.47 (24.60) | 87.18 (21.29) | 61.67 (24.01) |
| Role-Physical (RP) | 77.77 (36.20) | 86.61 (30.88) | 38.89 (37.60) |
| Bodily Pain (BP) | 73.59 (24.25) | 76.88 (22.97) | 39.22 (20.78) |
| General Health (GH) | 70.61 (21.50) | 73.48 (20.02) | 60.06 (22.37) |
| Vitality (VT) | 58.43 (21.47) | 63.59 (20.04) | 32.78 (22.44) |
| Social Functioning (SF) | 81.54 (21.47) | 85.23 (21.28) | 61.11 (24.21) |
| Role-Emotional (RE) | 79.47 (34.43) | 83.28 (31.31) | 53.70 (44.49) |
| Mental Health (MH) | 73.25 (18.68) | 76.37 (17.16) | 68.22 (15.85) |

The data presented in Table 2 are from Ware J E., SF-36 Health Survey: manual and interpretation guide. Boston, Mass.: Nimrod Press; 2:1–3:22 (1993); Schlenk EA, et al., Health-related quality of life in chronic disorders: a comparison across-studies using the MOS SF-36, *Quality Life Research*, 7:57–65 (1998)).

Although similarities in different categories of the MOS can be observed, data from patients who experience chronic conditions suggests that these patients may show higher variability when analyzing individual MOS categories than with the PCS and MCS summary scores. This variability may result from the frequent coexistence of chronic conditions. For example, it has been shown that 70% of patients with fibromyalgia also experience symptoms of irritable bowel syndrome (IBS), whereas only 10% of control patients experience IBS symptoms. (Veale D, et al., *Br J Rheumatol.*, 30:220–222 (1991)). Fibromyalgia patients have also been reported to shown similar symptoms as CFS.

Taking these considerations into accounts, Ware et al. have used principal component analysis on the MOS SF-36 data collected from 2,474 subjects from the U.S. general population to derive summary scores for the eight categories shown above. (Ware J E Jr., Kosinski M, Keller S D. SF-36 Physical & Mental Health Summary Scales: A user's manual. Boston, Mass.: The Health Institute, New England Medical Center; 3:1–4:6 (1994)). The Physical Component Summary (PCS) and Mental Component Summary (MCS) provide two reliable, reproducible scores for the physical and mental health, respectively. The PCS and MCS scores are converted to a scale of 0 to 100, in which 50 is the mean for the U.S. population.

This analysis of the MOS data takes into account the range of symptoms seen with the chronic condition and reduces the variability from individual patient differences. Low scores on the PCS indicate substantial limitations in self care, physical, social, and role activities, severe bodily pain, frequent tiredness, and health generally rated as poor, whereas high scores indicate no physical limitations, high energy level, and health generally rated as excellent. Low scores on the MCS indicate frequent psychological distress, substantial social and role disability due to emotional problems, and/or health generally rated as poor, whereas high scores indicate frequent positive affect and absence of psychological distress and limitations in usual social and role activities. Table 3 shows relative PCS and MCS scores for various chronic health conditions as compared to U.S. population normative data. Standard deviation is abbreviated as S.D.

TABLE 3

Comparison of Physical Component Summary (PCS) and Mental Component Summary (MCS) of the MOS SF-36 Questionnaire.

| Norms for US Population | Number of Respondents | Mean PCS Score (sd) | Mean MCS Score (sd) |
|---|---|---|---|
| Females | 1,412 | 49.07 (10.42) | 49.33 (10.32) |
| Males | 1,055 | 51.05 (9.39) | 50.73 (9.57) |
| "Healthy" individuals with no chronic conditions from US population | 465 | 55.26 (5.10) | 53.43 (6.33) |
| Individuals with self-reported depression symptoms | 881 | 47.92 (11.62) | 43.46 (11.42) |
| Individuals with Clinical Depression | 502 | 44.96 (12.05) | 34.84 (12.17) |
| Individuals with Arthritis | 826 | 43.15 (11.62) | 48.81 (11.11) |
| Individuals reporting chronic back pain | 519 | 43.14 (11.56) | 46.88 (11.73) |
| Individuals reporting allergies | 818 | 47.44 (10.81) | 48.23 (10.74) |
| Individuals with dermatitis or chronic skin rash | 214 | 46.88 (11.49) | 46.16 (12.06) |

It has been the experience of the present inventors that many patients with fatigue-related syndromes, such as fibromyalgia, respond with only moderate improvement to dietary programs. Further, this response has been variable, with a large percentage of patients with fatigue-related syndromes not responding to dietary changes at all. Pharmaceutical approaches, such as non-steroidal anti-inflammatories or anti-depressants have been investigated for fibromyalgia with moderate but variable response. In particular, research on the use of anti-inflammatories to treat fatigue-related syndromes has not shown significant improvement above placebo.

Consequently, there is a need for a dietary supplement and/or medical food that ameliorates at least one of the symptoms, preferably all of the symptoms of a fatigue-related syndrome, such as fibromyalgia, idiotypic fatigue, multiple chemical sensitivity and chronic fatigue syndrome, by way of example. In particular, there is a need for a dietary supplement and/or medical food that improves both the physical and mental functioning of a person suffering from a fatigue-related syndrome.

SUMMARY OF THE INVENTION

The present invention provides dietary supplements, medical foods and methods effective to ameliorate at least one of the symptoms, preferably all of the symptoms, of a fatigue-related syndrome, such as fibromyalgia, idiotypic fatigue, multiple chemical sensitivity and chronic fatigue syndrome. Preferred dietary supplements and medical foods of the present invention improve both the physical and mental functioning of a person suffering from a fatigue-related syndrome, such as fibromyalgia, idiotypic fatigue, multiple chemical sensitivity and chronic fatigue syndrome.

The dietary supplements of the present invention are compounded for the amelioration of a fatigue-related syndrome and include rosemary, curcumin and at least one component selected from the group consisting of quercetin and rutin. A presently preferred dietary supplement of the invention includes rosemary, curcumin and quercetin. The dietary supplements of the present invention are preferably compounded in a daily dose that includes rosemary in an amount of from about 180 mg to about 220 mg; curcumin in an amount of from about 360 mg to about 440 mg; quercetin, if utilized, in an amount of from about 360 mg to about 440 mg; and rutin, if utilized, in an amount of about 360 mg to about 440 mg.

Additionally, presently preferred dietary supplements of the invention may include at least one component selected from the group consisting of limonene, preferably D-limonene, hesperidin and ginger. The dietary supplements of the present invention are preferably compounded in a daily dose that can include one or more of the following components: limonene in an amount of from about 180 mg to about 220 mg; hesperidin in an amount of from about 360 mg to about 440 mg; and ginger in an amount of from about 180 mg to about 220 mg. The dietary supplements of the present invention optionally include at least one vitamin and at least one non-vitamin antioxidant.

The present invention also provides medical foods compounded for the amelioration of a fatigue-related syndrome. The medical foods of the present invention include rosemary, at least one macronutrient selected from the group consisting of protein, carbohydrate and fat, and at least one member of the group consisting of quercetin, curcumin and rutin. A presently preferred medical food of the invention includes rosemary, curcumin and quercetin. The medical foods of the present invention are preferably compounded in a daily dose that includes rosemary in an amount of from about 180 mg to about 220 mg; curcumin, if utilized, in an amount of from about 360 mg to about 440 mg; quercetin, if utilized, in an amount of from about 360 mg to about 440 mg; and rutin, if utilized, in an amount of about 360 mg to about 440 mg.

Additionally, presently preferred medical foods of the invention may include at least one component selected from the group consisting of limonene, preferably D-limonene, hesperidin and ginger. The medical foods of the present invention are preferably compounded in a daily dose that can include one or more of the following components: limonene in an amount of from about 180 mg to about 220 mg; hesperidin in an amount of from about 360 mg to about 440 mg; and ginger in an amount of from about 180 mg to about 220 mg. The medical foods of the present invention optionally include at least one vitamin and at least one non-vitamin antioxidant.

Macronutrients included in the medical foods of the present invention include protein, carbohydrates and fat. The protein is preferably obtained from a cereal grain that is gluten-free, or substantially gluten-free. The presently preferred protein source is a hypoallergenic rice protein concentrate, suitably prepared as disclosed in U.S. Pat. No. 4,876,096, incorporated herein by reference. A daily dose of the medical foods of the present invention include protein in an amount of from about 25 g to about 35 g. Carbohydrates are provided as rice fiber, bran and/or flour, or equivalent gluten-free or substantially gluten-free grain fiber, bran and/or flour. Carbohydrate can also be provided as rice syrup solids which contain approximately 70 to 90 percent by weight of high molecular weight dextran, or as equivalent gluten-free or substantially gluten-free grain syrup solids. A daily dose of the medical foods of the present invention include carbohydrate in an amount of from about 43 g to about 69 g. Fats are preferably provided as medium chain triglycerides, preferably in combination with canola oil. Canola oil can be substituted with nutritionally equivalent oils, such as flaxseed oil and safflower oil. Medium chain triglycerides useful in the compositions of the present invention include a fatty acid moiety having an 8 to 14 carbon atom backbone, and can be derived from, for example, coconut oil and related tropical oils. A daily dose of the medical foods of the present invention include fats in an amount of from about 3 g to about 8 g.

Presently preferred medical foods of the invention may also include at least one vitamin, or vitamin precursor. Preferred vitamins possess antioxidant properties and include vitamins A, C and E, and/or their biochemical precursors. Presently preferred medical foods of the invention also include at least one trace element, preferably selected from the group consisting of zinc, manganese and selenium. Presently preferred medical foods of the invention also may include at least one additional antioxidant selected from the group consisting of carotenoids, N-acetylcysteine and L-glutamine. The presently preferred amounts of preferred vitamins, trace elements, non-vitamin antioxidants and other components that can be included in the medical foods of the invention are set forth in Table 4.

In addition, the present invention provides methods for treating fatigue-related syndromes. In one embodiment, the methods of the present invention include the step of administering to a person suffering from a fatigue-related syndrome an effective amount of a dietary supplement of the present invention. Preferably the dietary supplement is administered at least once per day. In another embodiment, the methods of the present invention include the step of administering to a person suffering from a fatigue-related syndrome an effective amount of a medical food of the present invention. Preferably the medical food is administered at least once per day.

DETAILED DESCRIPTION OF THE PREFERRED EMBODIMENT

The present invention provides dietary supplements, medical foods and methods effective to ameliorate at least one of the symptoms of a fatigue-related syndrome. Preferred dietary supplements and medical foods of the present invention improve both the physical and mental functioning of a person suffering from a fatigue-related syndrome. As used herein, the term "fatigue-related syndrome" refers to a medical condition characterized by chronic fatigue. Typically, a person suffering from a fatigue-related syndrome exhibits other symptoms in addition to chronic fatigue, such as non-specific joint pain, muscle pain, headache, sleep disturbance, low-grade fever, lymphadenopathy, post-exertional fatigue, pharyngitis, impaired memory or concentration, and muscle weakness. As the term is used herein, a "fatigue-related syndrome" does not include inflammation as a predominant symptom. By way of non-limiting example, the term "fatigue-related syndrome" includes idiotypic fatigue, fibromyalgia, multiple chemical sensitivity and chronic fatigue syndrome. Presently preferred dietary supplements, medical foods and methods of the present invention are especially effective when used to treat fibromyalgia.

The compositions of the present invention include rosemary, curcumin (always present in the dietary supplements, optionally present in the medical foods) and at least one component selected from the group consisting of quercetin and rutin. Preferably rosemary is utilized as an extract of ground rosemary leaves; curcumin is utilized as a tumeric extract in powder form; quercetin is utilized as either pure quercetin or as a quercetin glycoside (e.g., rutin). The compositions of the present invention may preferably include ginger, limonene and hesperidin. Ginger is preferably utilized as a concentrate of a ginger root extract. Any pure, or substantially pure, form of limonene or hesperidin is useful in the compositions of the present invention.

Rosemary contains the flavonoids carnosol, carnosic acid, rosmanol and ursolic acid and the compositions of the present invention can be supplemented with one or more of the foregoing flavonoids. Ginger contains 6-gingerol, zingerone and 6-shogaol. The compositions of the present invention can be supplemented with one or more of the foregoing ginger components.

The medical foods of the present invention include a protein source, preferably hypoallergenic rice protein extract, suitably prepared as described in U.S. Pat. No. 4,876,096, incorporated herein by reference. The hypoallergenic rice protein extract is preferably fortified with at least one of the following amino acids: L-lysine, L-threonine and L-cysteine. In a presently preferred embodiment, the medical foods of the present invention are fortified with L-lysine and L-threonine in amounts of 6.3% and 0.28% of the weight of rice protein, respectively.

Both the dietary supplements and medical foods of the present invention are preferably used in powder form which can be dissolved in a liquid suitable for human consumption, such as water or a fruit juice. The dietary supplements and medical foods of the present invention can, however, be utilized in any suitable form, such as a solid bar, as a paste, gel, tablet, capsule or liquid.

Typically, the dietary supplements and medical foods of the present invention are preferably administered two times per day, preferably once in the morning and once in the afternoon. A typical treatment regime for the dietary supplements or medical foods will continue for four to eight weeks. Depending on such factors as the medical condition being treated and the response of the patient, the treatment regime may be extended. A medical food of the present invention will typically be consumed in two servings per day as either a meal replacement or as a snack between meals. A serving size for a medical food of the present invention will preferably be in the range of from about 45 grams to about 60 grams and will provide from about 180 calories to about 220 calories to the consumer. In a presently preferred treatment regime a person in need of treatment is provided with two servings of a medical food of the present invention per day. A presently preferred serving size is about 52 grams of powdered medical food which delivers about 200 calories to the consumer.

Suitable ranges for each component preferably included in a medical food in accordance with the present invention are set forth in Table 4 of Example 1. For a dietary supplement compounded in accordance with the present invention, the same ranges of specific ingredients to be included(e.g. Rosemary, Curcurmin, Quercetin, etc.) are utilized. The following examples merely illustrate a preferred embodiment now contemplated for practicing the invention, but should not be construed to limit the invention.

EXAMPLE 1

Improvement in PCS and MCS Components of the MOS SF-36 in Patients Treated with a Preferred Medical Food of the Present Invention Control Subjects: Sixteen subjects were included in the control, no-intervention study. These subjects were asked to complete a MOS questionnaire at the beginning of the study, and subsequently after an interval of between 1 to 15 weeks. Subjects were told to maintain their routines of diet, medication, and lifestyle and make no intentional changes in the intervening time. The control subjects varied in age from 39 to 61 years, with an average age of 49±7 years, and included 4 men and 12 women.

Subjects with fatigue-related syndromes: Five patients with primary symptoms relating to fatigue were evaluated with the intervention protocol for response. Subjects varied in age from 35 to 61 years, with an average age of 46±10 years, and included two men and three women.

Intervention Protocol: Control subjects received no intervention. Nutritional intervention for the subjects with fatigue-related syndromes involved supplementation of the daily diet with a presently preferred medical food of the invention described in Table 4 (Composition 1). Composition 1 was manufactured as a powdered drink mix, which was prepared by each subject at the time of use by mixing the appropriate amount of the composition in either water or a juice of the subject's choosing. Composition 1 was delivered in two servings per day of 52-gram size, which delivered 400 calories per day to the diet.

Intervention Protocol with Clinical Assessment: Subjects on the intervention protocols were provided with Composition 1 in a powdered form and a dietary protocol. The dietary changes prescribed in the dietary protocol consisted of a modified elimination diet, which is described as a diet free of substances known to produce allergenic responses and is preferably vegetarian. Subjects were instructed to make no changes in supplementation, medication, or exercise routine during the course of the intervention. Medications consumed by the subjects were documented at each office visit. Likewise, compliance to the protocol during the previous weeks was documented by questionnaire during the office visit.

Subjects were maintained on the protocol for between four and nine weeks. Subjects were evaluated by the MOS SF-36 questionnaire, a condition-specific questionnaire when appropriate, and a questionnaire to evaluate general physical symptoms called the Medical Symptoms Questionnaire (MSQ), described in Bland, J. S., and Bralley, J. A., Journal of Applied Nutrition 44: 2–15 (1992). Data were analyzed by standard statistical methods.

TABLE 4

Weight ranges for components of medical food of the invention and composition of presently preferred medical food of the invention (Composition 1).

| Nutrient | Units | Composition 1 | Range |
| --- | --- | --- | --- |
| Rice protein | grams | 30 | 25–35 |
| Rice fiber | grams | 8 | 7–9 |
| Rice carbohydrates | grams | 48 | 43–53 |
| Vegetable Oil | grams | 3.34 | 3–4 |
| Medium-chain tryglycerides | grams | 3.34 | 3–4 |
| Vitamin A (mixed carotenoids/palmitate) | IU | 10,000 | 9,000–11,000 |
| Vitamin C | mg | 360 | 320–400 |
| Calcium | mg | 550 | 500–600 |
| Vitamin D | IU | 200 | 180–220 |
| Vitamin E | IU | 200 | 180–220 |
| Thiamin (B1) | mg | 4 | 3–5 |
| Riboflavin (B2) | mg | 4 | 3–5 |
| Niacin (B3) | mg | 70 | 60–80 |
| Vitamin B6 | mg | 10 | 8–12 |
| Folic acid | μg | 160 | 140–180 |
| Vitamin B12 | mcg | 6 | 5–7 |
| Biotin | mcg | 300 | 270–330 |
| Pantothenic Acid | mg | 10 | 8–12 |
| Phosphorous | mg | 400 | 360–440 |
| Magnesium | mg | 560 | 500–600 |
| Zinc | mg | 20 | 18–22 |
| Selenium | mcg | 150 | 140–160 |
| Copper | mg | 2 | 1.5–2.5 |
| Manganese | mg | 4 | 3.5–4.5 |
| Chromium | mcg | 120 | 100–140 |
| N-acetyl cysteine (NAC) | mg | 200 | 180–220 |
| Sodium sulfate | mg | 100 | 80–120 |
| Molybdenum | mcg | 76 | 65–85 |
| L-glutamine | mg | 1500 | 1200–1800 |
| L-threonine | mg | 68 | 60–75 |
| L-lysine HCl | mg | 1540 | 1200–1800 |
| Citrulline | mg | 200 | 180–220 |
| Hesperidin | mg | 400 | 360–440 |
| Quercetin | mg | 400 | 360–440 |
| Rutin | mg | 400 | 360–440 |
| Curcumin | mg | 400 | 360–440 |
| Rosemary | mg | 200 | 180–220 |
| D-limonene | mg | 200 | 180–220 |
| Ginger | mg | 200 | 180–220 |

Changes with no intervention: The changes in MOS SF-36 responses was evaluated over time with no intervention. In Table 5, the average change in score in the eight MOS categories is seen to be seven or less points in the 16 control subjects. In Table 6, the summary PCS and MCS scores for the control subjects are shown, which also reveal that the summary scores remain consistent over the course of 4±3 weeks.

TABLE 5

Summary of the Eight Categories of the SF-36 in 16 Subjects With no Intervention (Average Intervening Time Between Initial Score and Final Score Was 4 ± 3 Weeks).

| | Initial Score | Final Score | Average Change in Score |
| --- | --- | --- | --- |
| Physical Functioning | 60 ± 30 | 64 ± 32 | −4 ± 17 |
| Role-Physical | 41 ± 39 | 44 ± 40 | −3 ± 38 |
| Bodily Pain | 55 ± 21 | 50 ± 26 | 5 ± 21 |
| General Health | 54 ± 24 | 50 ± 21 | 4 ± 16 |
| Vitality | 31 ± 19 | 38 ± 15 | −7 ± 11 |
| Social Function | 66 ± 27 | 62 ± 24 | 4 ± 26 |
| Role-Emotional | 53 ± 43 | 51 ± 43 | 2 ± 42 |
| Mental Health | 60 ± 20 | 64 ± 11 | −4 ± 18 |

TABLE 6

Physical Component Summary (PCS) and Mental Component Summary (MCS) Scores From the MOS SF-36 in 16 Subjects With no Intervention (Average Intervening Time Was 4 ± 3 Weeks)

| | Physical Component Summary (PCS) | | | Mental Component Summary (MCS) | | |
| --- | --- | --- | --- | --- | --- | --- |
| | Initial Score | Final Score | Change | Initial Score | Final Score | Change |
| Average (sd) | 39 ± 11 | 39 ± 13 | 0.34 ± 7.9 | 43 ± 13 | 42 ± 8.4 | 0.51 ± 9.9 |

Data obtained from subjects with fatigue-related syndromes who received the nutritional intervention are shown below. In Table 7 the average change per individual category of the MOS SF-36 is shown. In Table 8, the primary complaint(s) and weeks on the protocol are shown, as well as the PCS and MCS Scores In this series of studies, significant improvement was observed in the categories of the MOS-SF-36 that evaluate mental functioning and fatigue. The categories of the MOS SF-36 that showed the most improvement were Social Functioning and Role Emotional. The MCS score was also significantly increased, from 40 points to 53 points.

TABLE 7

Summary of the Eight Categories of the MOS SF-36 in Five Subjects With Fatigue-Related Syndromes Before and After Intervention with Composition 1.

| | Initial Score | Final Score | Average Change in Score |
| --- | --- | --- | --- |
| Physical Functioning | 74 ± 20 | 75 ± 17 | 1.0 ± 6.5 |
| Role-Physical | 40 ± 45 | 55 ± 41 | 15 ± 38 |
| Bodily Pain | 51 ± 10 | 54 ± 16 | 2.4 ± 18 |
| General Health | 63 ± 16 | 66 ± 22 | 3.6 ± 13 |
| Vitality | 42 ± 26 | 54 ± 22 | 12 ± 14 |
| Social Function | 53 ± 40 | 85 ± 16 | 33 ± 45 |
| Role-Emotional | 40 ± 43 | 93 ± 15 | 53 ± 45 |
| Mental Health | 66 ± 14 | 69 ± 19 | 2.4 ± 17 |

TABLE 8

The Physical Component Summary (PCS) and Mental Component Summary (MCS) from Five Subjects With Fatigue-Related Syndrome Before and After Intervention With Composition 1.

| Patient Code | Major Symptoms | Weeks | Physical Component Summary (PCS) | | | Mental Component Summary (MCS) | | |
|---|---|---|---|---|---|---|---|---|
| | | | Initial Score | Final Score | Change | Initial Score | Final Score | Change |
| 45 | idiotypic fatigue, non-specific joint pain | 8 | 48 | 45 | −2.9 | 52 | 68 | 16 |
| 134 | fibromyalgia, atypical colitis | 8 | 36 | 39 | 2.8 | 42 | 52 | 10 |
| 17 | fatigue, mood swings | 4 | 49 | 48 | −0.90 | 26 | 48 | 22 |
| 331 | multiple chemical sensitivity | 8 | 52 | 52 | −0.18 | 35 | 52 | 17 |
| 341 | unremitting fatigue, chronic fatigue syndrome | 6 | 28 | 26 | −2.7 | 45 | 47 | 2.2 |
| Ave (sd) | | 7 ± 2 | 43 ± 10 | 42 ± 10 | −0.77 ± 2.3 | 40 ± 10 | 53 ± 8.3 | 13 ± 7.6 |

EXAMPLE 2

Improvement in the MCS and PCS Scores of Fibromyalgia Patients Treated with a Presently Preferred Medical Food of the Invention Trial Subjects: Twenty-six subjects were selected on the basis of past diagnosis of fibromyalgia, presentation with chronic musculoskeletal pain of greater than six months duration, and reports of unrestorative or disturbed sleep as assessed by a symptoms questionnaire. Subjects were female with an average age of 47 years, and a range in age of 29 to 65 years. The majority of subjects reported experiencing fibromyalgia symptoms for more than five years, and all subjects reported experiencing symptoms for at least 1–2 years.

Intervention Protocol: Nutritional intervention involved the supplementation of daily diets with one of three different nutritional compositions for a six week period. The amount of nutrients delivered each day by the nutritional compositions is indicated in Table 9. Nutritional compositions were manufactured as a powder drink mix which was prepared by each subject at the time of use. Nutritional compositions were prepared by mixing the appropriate amount of the composition in either water or a juice of the subject's choosing. Composition 1 (a presently preferred medical food of the present invention) was delivered in two 52 gram servings per day for a total of 400 calories per day. Compositions 2 and 3 were each delivered in three 44 gram servings per day for a total of 480 calories per day. Subjects were randomized by trial entry date to one of four different intervention protocols:

The four intervention protocols were: Protocol 1: Composition 1 with no other dietary changes; Protocol 2: Composition 1 with dietary changes; Protocol 3: Composition 2 with dietary changes; Protocol 4: Composition 3 with dietary changes.

Dietary changes consisted of a modified elimination diet, which is a diet free of substances known to produce allergenic responses and is preferably vegetarian. Subjects were instructed to make no changes in their supplementation or medication or exercise routine during the study. Medications consumed by the subjects were documented at each office visit. Likewise, compliance with the protocol during the previous weeks was documented by questionnaire during the office visit.

Clinical Assessment: Subjects were evaluated initially, then at three weeks and at six to eight weeks by questionnaire, documentation of tender points, and grip strength test. Questionnaires included the MOS SF-36 questionnaire, a condition-specific questionnaire, which evaluated sleep patterns, perceived pain and functioning, medication use, and compliance to the protocol, and the Medical Symptoms Questionnaire (MSQ) which evaluated general physical symptoms. Data were analyzed by standard statistical methods. In Tables 10–16, "before intervention" means at the beginning of the trial, and "after intervention" means after six to eight weeks of treatment.

TABLE 9

Composition of the Nutritional Supplements

| | | Amount per day in composition | | |
|---|---|---|---|---|
| Nutrients | Units | Composition 1 | Composition 2 | Composition 3 |
| Rice protein | grams | 30 | 51 | 45 |
| Rice fiber | grams | 8 | 0 | 0 |
| Rice carbohydrates | grams | 48 | 57 | 57 |
| Vegetable Oil | grams | 3.34 | 2.56 | 2.56 |
| Medium-chain tryglycerides | grams | 3.34 | 2.56 | 2.56 |
| Vitamin A (mixed carotenoids/palmitate) | IU | 10,000 | 4500 | 15,000 |
| Vitamin C | mg | 360 | 0 | 1200 |
| Calcium | mg | 550 | 0 | 600 |
| Iron | mg | 2 | 0 | 10.8 |
| Vitamin D | IU | 200 | 0 | 240 |

TABLE 9-continued

Composition of the Nutritional Supplements

| | | Amount per day in composition | | |
|---|---|---|---|---|
| Nutrients | Units | Composition 1 | Composition 2 | Composition 3 |
| Vitamin E | IU | 200 | 0 | 492 |
| Thiamin (B1) | mg | 4 | 0 | 36 |
| Riboflavin (B2) | mg | 4 | 6 | 36 |
| Niacin (B3) | mg | 70 | 0 | 21 |
| Vitamin B6 | mg | 10 | 0 | 10.2 |
| Folic Acid | µg | 160 | 0 | 240 |
| Vitamin B12 | mcg | 6 | 0 | 10.8 |
| Biotin | mcg | 300 | 0 | 405 |
| Pantothenic Acid | mg | 10 | 0 | 108 |
| Phosphorous | mg | 400 | 0 | 600 |
| Iodine | mcg | 0 | 0 | 159 |
| Magnesium | mg | 560 | 0 | 900 |
| Zinc | mg | 20 | 0 | 30 |
| Selenium | mcg | 150 | 0 | 120 |
| Copper | mg | 2 | 0 | 3 |
| Manganese | mg | 4 | 0 | 3.9 |
| Chromium | mcg | 120 | 0 | 150 |
| L-glutathione | mg | 0 | 0 | 330 |
| L-cysteine | mg | 0 | 0 | 15 |
| NAC | mg | 200 | 0 | 360 |
| Glycine | mg | 0 | 0 | 4800 |
| Taurine | mg | 0 | 0 | 300 |
| Sodium sulfate | mg | 100 | 0 | 90 |
| Catechins | mg | 0 | 0 | 45 |
| Creatine | mg | 0 | 0 | 600 |
| N-acetyl-carnitine | mg | 0 | 0 | 180 |
| CoQ 10 | mg | 0 | 0 | 30 |
| L-isoleucine | mcg | 0 | 0 | 1350 |
| Red grape skin | mg | 0 | 0 | 30 |
| Molybdenum | mcg | 76 | 0 | 0 |
| L-glutamine | mg | 1500 | 0 | 0 |
| L-threonine | mg | 68 | 102 | 0 |
| L-lysine HCl | mg | 1540 | 102 | 0 |
| Citrulline | mg | 200 | 0 | 0 |
| Hesperidin | mg | 400 | 0 | 0 |
| Quercetin | mg | 400 | 0 | 0 |
| Curcumin | mg | 400 | 0 | 0 |
| Rosemary Antioxidants | mg | 200 | 0 | 0 |
| D-limonene | mg | 200 | 0 | 0 |
| Rutin | mg | 400 | 0 | 0 |
| Ginger | mg | 200 | 0 | 0 |

Table 10 sets forth a summary of the eight categories of the SF-36 in 18 fibromyalgia subjects treated with nutritional composition 1 with no diet changes.

TABLE 10

Summary of the Eight Categories of the SF-36 in 18 Fibromyalgia Subjects Treated With Nutritional Composition 1 with no Diet Changes.

| | Before Intervention | After Intervention | Average Change in Score |
|---|---|---|---|
| Physical Functioning | 51 ± 24 | 67 ± 19 | +16 ± 13 |
| Role-Physical | 0.0 ± 0.0 | 44 ± 44 | +44 ± 44 |
| Bodily Pain | 36 ± 15 | 53 ± 16 | +17 ± 20 |
| General Health | 32 ± 10 | 54 ± 16 | +22 ± 11 |
| Vitality | 21 ± 14 | 49 ± 14 | +29 ± 21 |
| Social Function | 55 ± 26 | 81 ± 13 | +23 ± 36 |
| Role-Emotional | 25 ± 15 | 62 ± 42 | +38 ± 45 |
| Mental Health | 60 ± 119 | 81 ± 8 | +20 ± 18 |

Table 11 sets forth a summary of the eight categories of the SF-36 in 6 fibromyalgia subjects treated with nutritional Composition 1 and diet changes.

TABLE 11

Summary of the Eight Categories of the SF-36 in 6 Fibromyalgia Subjects Treated with Nutritional Composition 1 and Diet Changes.

| | Before Intervention | After Intervention | Average Change in Score |
|---|---|---|---|
| Physical Functioning | 33 ± 27 | 36 ± 21 | +3 ± 34 |
| Role-Physical | 13 ± 21 | 21 ± 40 | +8 ± 20 |
| Bodily Pain | 25 ± 14 | 43 ± 24 | +19 ± 29 |
| General Health | 41 ± 17 | 42 ± 27 | −1 ± 26 |
| Vitality | 23 ± 12 | 44 ± 22 | +17 ± 26 |
| Social Function | 42 ± 27 | 75 ± 23 | +31 ± 30 |
| Role-Emotional | 44 ± 46 | 61 ± 33 | +17 ± 35 |
| Mental Health | 55 ± 25 | 84 ± 7 | +19 ± 3 |

Table 12 sets forth a summary of the eight categories of the SF-36 in six fibromyalgia subjects treated with nutritional composition 2 and diet changes.

TABLE 12

Summary of the Eight Categories of the SF-36 in Six Fibromyalgia Subjects Treated with Nutritional Composition 2 and Diet Changes.

| | Before Intervention | After Intervention | Average Change in Score |
|---|---|---|---|
| Physical Functioning | 27 ± 22 | 40 ± 28 | +13 ± 29 |
| Role-Physical | 4 ± 10 | 0.0 ± 0.0 | −4 ± 10 |
| Bodily Pain | 25 ± 16 | 31 ± 21 | +6 ± 18 |
| General Health | 23 ± 13 | 22 ± 11 | −1 ± 7 |
| Vitality | 34 ± 16 | 28 ± 18 | −6 ± 20 |
| Social Function | 27 ± 18 | 27 ± 20 | 0 ± 8 |
| Role-Emotional | 6 ± 14 | 17 ± 41 | +11 ± 45 |
| Mental Health | 64 ± 15 | 61 ± 19 | −3 ± 13 |

Table 13 sets forth a summary of the eight categories of the SF-36 in six fibromyalgia subjects with nutritional composition 3 and diet changes.

TABLE 13

Summary of the Eight Categories of the SF-36 in Six Fibromyalgia Subjects with Nutritional Composition 3 and Diet Changes.

| | Before Intervention | After Intervention | Average Change in Score |
|---|---|---|---|
| Physical Functioning | 44 ± 28 | 50 ± 30 | +6 ± 14 |
| Role-Physical | 4 ± 10 | 21 ± 40 | +17 ± 30 |
| Bodily Pain | 25 ± 21 | 31 ± 18 | +7 ± 18 |
| General Health | 25 ± 26 | 34 ± 28 | −1 ± 12 |
| Vitality | 23 ± 30 | 25 ± 27 | +3 ± 17 |
| Social Function | 38 ± 22 | 52 ± 28 | 15 ± 24 |
| Role-Emotional | 6 ± 14 | 39 ± 39 | +33 ± 42 |
| Mental Health | 59 ± 14 | 55 ± 24 | −4 ± 23 |

Table 14 sets forth the physical component summary (PCS) and mental component summary (MCS) of the MOS SF-36 for fibromyalgia patients treated with composition 1, 2 or 3.

TABLE 14

Physical Component Summary (PCS) and Mental Component Summary (MCS) of the MOS SF-36 for Fibromyalgia Patients Treated with Composition 1, 2 or 3.

|  | Physical Component Summary (PCS) | | Mental Component Summary (MCS) | |
| --- | --- | --- | --- | --- |
|  | Before Intervention | After Intervention | Before Intervention | After Intervention |
| Fibromyalgia patients treated with Composition 1 and no diet changes (n = 8) | 29.76 ± 6.77 | 37.87 ± 5.74 | 39.62 ± 8.39 | 51.66 ± 8.48 |
| Fibromyalgia patients treated with Composition 1 and diet changes (n = 6) | 26.84 ± 8.64 | 27.19 ± 10.78 | 40.43 ± 13.65 | 52.33 ± 2.99 |
| Fibromyalgia patients treated with Composition 2 and diet changes (n = 6) | 23.93 ± 6.14 | 25.9 ± 9.51 | 38.40 ± 5.91 | 37.09 ± 11.26 |
| Fibromyalgia patients treated with Composition 3 and diet changes (n = 6) | 29.04 ± 11.41 | 31.12 ± 10.70 | 35.23 ± 4.94 | 39.10 ± 12.76 |

Table 15 sets forth a summary of tender points in fibromyalgia patients before and after nutritional intervention with compositions 1, 2, and 3. The population of fibromyalgia patients treated with Composition 1 included a group of patients who had no other dietary changes, and a group of patients who had other dietary changes. Fisher's Exact test was applied to the two groups (with and without dietary changes) and no significant difference was observed between the two groups. Consequently, the data from the two groups was pooled for subsequent analysis as set forth in Tables 15–17.

TABLE 15

Tender Points In Fibromyalgia Patients Before And After Nutritional Intervention With Compositions 1, 2, and 3.

|  | Tender Point Index (maximum = 18 TP) | | |
| --- | --- | --- | --- |
|  | Before Intervention | After Intervention | Summary |
| Fibromyalgia patients treated with Composition 1, with and without diet changes (n = 14) | 12.2 ± 3.8 | 9.4 ± 4.7 | Decreased by 3 Tender Points |
| Fibromyalgia patients treated with Composition 2, and with diet changes (n = 5) | 7.4 ± 2.1 | 7.4 ± 2.1 | No Change |
| Fibromyalgia patients treated with Composition 3, and with diet changes. | 8.2 ± 1.0 | 8.2 ± 1.0 | No Change |

Table 16 sets forth grip strength in fibromyalgia patients before and after nutritional intervention with composition 1.

TABLE 16

Grip Strength in Fibromyalgia Patients Before and After Nutritional Intervention With Composition 1.

|  | Right Hand Grip Strength | | Left Hand Grip Strength | |
| --- | --- | --- | --- | --- |
|  | Before Intervention | After Intervention | Before Intervention | After Intervention |
| Fibromyalgia patients treated with Composition 1, and with and without diet changes (n = 14) | 25 ± 7.5 | 29 ± 6.7 | 21 ± 5.3 | 24 ± 5.6 |

Table 17 sets forth the results of a medical symptoms questionnaire (MSQ) in fibromyalgia patients before and after nutritional intervention with compositions 1, 2, and 3. In contrast to the MOS SF-36, in which a higher number indicates a healthier subject, a higher number in the MSQ indicates the presence of a higher number and/or intensity of symptoms. Consequently, a lower MSQ score indicates a healthier subject.

TABLE 17

Medical Symptoms Questionnaire (MSQ) In Fibromyalgia Patients Before And After Nutritional Intervention With Compositions 1, 2, And 3.

|  | MSQ (maximum total points = 180) | |
| --- | --- | --- |
|  | Before Intervention | After Intervention |
| Fibromyalgia patients treated with Composition 1, with and without diet changes (n = 14) | 101 ± 32 | 59 ± 34 |
| Fibromyalgia patients treated with Composition 2, with diet changes (n = 6) | 125 ± 40 | 98 ± 38 |
| Fibromyalgia patients treated with Composition 3, with diet changes (n = 6) | 109 ± 78 | 78 ± 40 |

Composition 1 resulted in significant improvement in the MCS section of the MOS SF-36 in fibromyalgia patients. This result indicates improved clinical outcome with respect to mental well-being. The improvement in mental well-being observed with Composition 1 was not dependent on whether dietary changes accompanied the nutrient supplementation protocol, since both groups who received Composition 1, those who made dietary changes and those who did not, showed significant improvement.

Composition 1 also resulted in substantial improvement in physical functioning as observed by decreased tender point index, improved grip strength, and decreased symptoms index on the MSQ. Furthermore, improvement in physical parameters was also seen with Composition 1, in particular with Composition 1 when no dietary intervention was included in the protocol. Compositions 2 and 3 did not result in similar improvements.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A dietary supplement comprising rosemary, curcumin and at least one additional component selected from the group consisting of quercetin and rutin, said dietary supplement compounded for the amelioration of a fatigue-related syndrome.

2. The dietary supplement of claim 1 comprising rosemary, curcumin and rutin.

3. The dietary supplement of claim 1 comprising rosemary, curcumin and quercetin.

4. The dietary supplement of claim 1 comprising rosemary, curcumin, rutin and quercetin.

5. The dietary supplement of claim 1 further comprising at least one additional component selected from the group consisting of limonene, hesperidin and ginger.

6. The dietary supplement of claim 1 further comprising a trace element selected from the group consisting of zinc, manganese and selenium.

7. The dietary supplement of claim 1 further comprising a vitamin.

8. The dietary supplement of claim 1 further comprising a non-vitamin antioxidant.

9. The dietary supplement of claim 2 wherein the supplement is compounded in a daily dose comprising rosemary present in an amount of from about 180 milligrams to about 220 milligrams, curcumin present in an amount of from about 360 milligrams to about 440 milligrams and rutin present in an amount of from about 360 milligrams to about 440 milligrams.

10. The dietary supplement of claim 3 wherein the supplement is compounded in a daily dose comprising rosemary present in an amount of from about 180 milligrams to about 220 milligrams, curcumin present in an amount of from about 360 milligrams to about 440 milligrams and quercetin present in an amount of from about 360 milligrams to about 440 milligrams.

11. The dietary supplement of claim 4 wherein the supplement is compounded in a daily dose comprising rosemary present in an amount of from about 180 milligrams to about 220 milligrams, curcumin present in an amount of from about 360 milligrams to about 440 milligrams, rutin present in an amount of from about 360 milligrams to about 440 milligrams, and quercetin present in an amount of from about 360 milligrams to about 440 milligrams.

12. A medical food comprising rosemary, at least one macronutrient selected from the group consisting of protein, carbohydrate and fat, and at least one member of the group consisting of quercetin, curcumin and rutin, said medical food compounded for the amelioration of a fatigue-related syndrome.

13. The medical food of claim 12 comprising rosemary and curcumin.

14. The medical food of claim 12 comprising rosemary and quercetin.

15. The medical food of claim 12 comprising rosemary, curcumin and quercetin.

16. The medical food of claim 12 further comprising a vitamin and a non-vitamin antioxidant.

17. The medical food of claim 12 further comprising limonene, hesperidin and ginger.

18. The medical food of claim 12 wherein the protein is substantially gluten free.

19. The medical food of claim 18 wherein the protein is a hypoallergenic rice protein extract.

20. The medical food of claim 12 wherein the carbohydrate is a member of the group consisting of rice fiber, rice bran, rice syrup and rice flour.

21. The medical food of claim 12 wherein the fat comprises at least one medium chain triglyceride.

22. A method for treating fatigue-related syndromes comprising administering to a person suffering from a fatigue-related syndrome an effective amount of a dietary supplement comprising rosemary and at least one additional component selected from the group consisting of quercetin, curcumin and rutin.

23. The method of claim 22 wherein the dietary supplement comprises rosemary and curcumin.

24. The method of claim 22 wherein the dietary supplement comprises rosemary and quercetin.

25. The method of claim 22 wherein the dietary supplement comprises rosemary, curcumin and quercetin.

26. The method of claim 22 wherein the dietary supplement further comprises limonene, hesperidin and ginger.

27. The method of claim 23 wherein the dietary supplement is compounded in a daily dose comprising rosemary present in an amount of from about 180 milligrams to about 220 milligrams and curcumin present in an amount of from about 360 milligrams to about 440 milligrams.

28. The method of claim 24 wherein the dietary supplement is compounded in a daily dose comprising rosemary present in an amount of from about 180 milligrams to about 220 milligrams and quercetin present in an amount of from about 360 milligrams to about 440 milligrams.

29. The method of claim 25 wherein the dietary supplement is compounded in a daily dose comprising rosemary present in an amount of from about 180 milligrams to about 220 milligrams, curcumin present in an amount of from about 360 milligrams to about 440 milligrams and quercetin present in an amount of from about 360 milligrams to about 440 milligrams.

30. A method for treating fatigue-related syndromes comprising administering to a person suffering from a fatigue-related syndrome an effective amount of a medical food comprising rosemary, at least one macronutrient selected from the group consisting of protein, carbohydrate and fat, and at least one additional component selected from the group consisting of quercetin, curcumin and rutin.

31. The method of claim 30 wherein the medical food comprises rosemary and curcumin.

32. The method of claim 30 wherein the medical food comprises rosemary and quercetin.

33. The method of claim 30 wherein the medical food comprises rosemary, curcumin and quercetin.

34. The method of claim 30 wherein the medical food further comprises limonene, hesperidin and ginger.

35. The method of claim 31 wherein the medical food is compounded in a daily dose comprising rosemary present in an amount of from about 180 milligrams to about 220 milligrams and curcumin present in an amount of from about 360 milligrams to about 440 milligrams.

36. The method of claim 32 wherein the medical food is compounded in a daily dose comprising rosemary present in an amount of from about 180 milligrams to about 220 milligrams and quercetin present in an amount of from about 360 milligrams to about 440 milligrams.

37. The method of claim 32 wherein the medical food is compounded in a daily dose comprising rosemary present in an amount of from about 180 milligrams to about 220 milligrams, curcumin present in an amount of from about 360 milligrams to about 440 milligrams and quercetin present in an amount of from about 360 milligrams to about 440 milligrams.

38. The method of claim 30 wherein the protein is a hypoallergenic rice protein.

39. A dietary supplement comprising rosemary, curcumin and at least one additional component selected from the group consisting of quercetin, rutin, limonene, hesperidin and ginger, said dietary supplement compounded for the amelioration of a fatigue-related syndrome.

40. A medical food comprising rosemary, at least one macronutrient selected from the group consisting of protein, carbohydrate and fat, and at least one additional component selected from the group consisting of quercetin, curcumin, rutin, limonene, hesperidin and ginger, said medical food compounded for the amelioration of a fatigue-related syndrome.

* * * * *